(12) United States Patent
Kawamura (10) Patent No.: US 9,522,250 B2
(45) Date of Patent: Dec. 20, 2016

(54) HYDROGEN-RICH GAS MIXTURE BREATHING SYSTEM

(71) Applicant: Takao Kawamura, Tokyo (JP)

(72) Inventor: Takao Kawamura, Tokyo (JP)

(*) Notice: Subject to any disclaimer, the term of this patent is extended or adjusted under 35 U.S.C. 154(b) by 0 days.

(21) Appl. No.: 14/915,054

(22) PCT Filed: Aug. 19, 2014

(86) PCT No.: PCT/JP2014/071666
§ 371 (c)(1),
(2) Date: Feb. 26, 2016

(87) PCT Pub. No.: WO2015/029838
PCT Pub. Date: Mar. 5, 2015

(65) Prior Publication Data
US 2016/0199603 A1    Jul. 14, 2016

(30) Foreign Application Priority Data

Sep. 1, 2013   (JP) .................................. 2013-180812

(51) Int. Cl.
*A61M 16/00* (2006.01)
*A61M 16/12* (2006.01)
(Continued)

(52) U.S. Cl.
CPC ............ *A61M 16/12* (2013.01); *A61M 11/001* (2014.02); *A61M 16/0087* (2013.01);
(Continued)

(58) Field of Classification Search
CPC .. A61M 11/001; A61M 16/009; A61M 16/06; A61M 16/122; A61M 16/14; A61M 16/22; A61M 2202/02; A61M 2202/0468; A61M 16/12; A61M 16/0087
See application file for complete search history.

(56) References Cited

U.S. PATENT DOCUMENTS 3,914,002 A * 10/1975 Berliner ............ A61M 16/0087
174/47
5,678,540 A 10/1997 Kock et al.
(Continued)

FOREIGN PATENT DOCUMENTS

CN  1795362   6/2006
CN  102974021  3/2013
(Continued)

OTHER PUBLICATIONS

International Search Report for PCT/JP2014/071666, dated Nov. 25, 2014, and English translation thereof, 4 pages total.
(Continued)

*Primary Examiner* — Bradley Philips
(74) *Attorney, Agent, or Firm* — Hamre, Schumann, Mueller & Larson, P.C.

(57) ABSTRACT

The objective of the present invention is to allow a hydrogen gas which has a gas mixture concentration of over 4% to be breathed in safely, and to reduce the amount of use of hydrogen gas, which is dangerous, and increase utilization efficiency of the hydrogen gas. The objective of the present invention is also to impart an auxiliary role to a device in the treatment of patients suffering from viral or bacterial pneumonia using hydrogen gas. A hydrogen gas mixture breathing device and a related system employ an intrinsically safe structure and a safety system which prevent occurrence of explosions. A detonation flame arrester, etc. are installed where necessary to provide against electrostatic explosions, etc., and to protect a user's lung function from explosion flames. In addition, a device for supplying aerosol in which a hydroxyl radical is dissolved is also installed, and operating time and volume are appropriately adjusted under the supervision of a professional. Depending on the circumstances, the content of the aerosol is changed to microdroplets that comprise a bivalent iron ion or monovalent copper
(Continued)

Normal Pressure Forced Circulation-Type Hydrogen-rich Gas Mixture Breathing System
(constituted by Intrinsically Safe Explosion-Preventive Structure)
(Highly Oxidizing Aerosol Supply Device Including-Type)

ion. Suction of a hydrogen-rich gas mixture and suction of the aerosol take place alternatively according to a program and not simultaneously.

13 Claims, 7 Drawing Sheets (51) Int. Cl.
A61M 11/00 (2006.01)
A61M 16/06 (2006.01)
A61M 16/14 (2006.01)
A62C 4/00 (2006.01)
A61M 15/02 (2006.01)
A61M 16/08 (2006.01)
A61M 16/22 (2006.01)
A61M 16/10 (2006.01)
A61M 16/16 (2006.01)
A61M 16/20 (2006.01)
A61K 9/00 (2006.01)

(52) U.S. Cl.
CPC ........ A61M 16/06 (2013.01); A61M 16/0891 (2014.02); A61M 16/122 (2014.02); A61M 16/14 (2013.01); A62C 4/00 (2013.01); A61K 9/0073 (2013.01); A61M 15/02 (2013.01); A61M 16/009 (2013.01); A61M 16/0045 (2013.01); A61M 16/0078 (2013.01); A61M 16/0808 (2013.01); A61M 16/161 (2014.02); A61M 16/202 (2014.02); A61M 16/22 (2013.01); A61M 2016/0027 (2013.01); A61M 2016/102 (2013.01); A61M 2202/02 (2013.01); A61M 2202/0468 (2013.01); A61M 2205/15 (2013.01); A61M 2205/3368 (2013.01); A61M 2205/3389 (2013.01); A61M 2230/205 (2013.01); A61M 2230/43 (2013.01)

(56) References Cited

U.S. PATENT DOCUMENTS

2004/0216743 A1* 11/2004 Orr .................. A61M 16/0045
                                                    128/205.12
2013/0177653 A1* 7/2013 Ohta ........................ A23L 1/30
                                                    424/600
2015/0144132 A1* 5/2015 Satoh ................ A61M 16/0057
                                                    128/202.26

FOREIGN PATENT DOCUMENTS

| JP | 07-265428 | 10/1995 |
| JP | 2001-516015 | 9/2001 |
| JP | 2004-144564 | 5/2004 |
| JP | 2005-526576 | 9/2005 |
| JP | 2008-190669 | 8/2008 |
| JP | 2009-005881 | 1/2009 |
| JP | 5106110 | 12/2012 |
| JP | 5228142 | 7/2013 |
| WO | 99/09388 | 2/1999 |
| WO | 03/099364 | 12/2003 |
| WO | 2007/021034 | 2/2007 |
| WO | 2013/138905 | 9/2013 |

OTHER PUBLICATIONS

Ohta et al., "Anti-oxidant treatment method and preventive medicine of new concept using hydrogen molecules," Experimental Medicine, vol. 26, No. 13, 2008, pp. 2074-2080.

* cited by examiner

FIG. 1

Normal Pressure Forced Circulation-Type Hydrogen-rich Gas Mixture Breathing System
(constituted by Intrinsically Safe Explosion-Preventive Structure)
(Highly Oxidizing Aerosol Supply Device Including-Type)

FIG. 2

Normal Pressure Forced Circulation-Type Hydrogen-rich Gas Mixture Breathing System
(constituted by Intrinsically Safe Explosion-Preventive Structure)
(Highly Oxidizing Aerosol Supply Device Including-Type)

FIG. 3

Schematic Explanatory View of Hydrogen-rich Gas Mixture Breathing System
(System constituted by intrinsically safe explosion-preventive structure)

FIG. 4

Saturated vapor partial pressure: 47 Torr/760 Torr (atmospheric pressure)
Temperature and Humidity of Breathing Gas

FIG. 5

Principle of Detonation Flame Arrester

FIG. 6

Made of porous sintered alloy or stacked porous metal fibers
Thickness t = 1 to 2 mm, Average pore diameter: about 10 to 30μm

In the case of general adults
Blood Amount     At the time of rest     At the time of exercise
                 (5L/min)           to    (25L/min)
The blood amount accounts for about 8% of the body weight, and the
blood is composed of a corpuscle component and a plasma
component, with water component accounting for about 50%.

Breathing (at the time of rest) about 500mL/time per one suction
                                12 to 20 breathing times per minute
Amount of breathing per minute: about 6.0L to 10.0L Quantitative Outline between Breathing and Blood Circulation in Human Body
(For Use in Simple Calculation at the time of Suction of Hydrogen Mixed Gas)

FIG. 10

In the case of general adults

Supposing that the body weight is 70kg, with the water component of the body assumed to be 60%, that is, 70kg × 60% = 42kg, and supposing that 42kg = 42L, the maximum dissolved amount of hydrogen gas to be dissolved is represented by: 0.00162g (value at 20°C) × 42L (water component of the body) × 92% (corrected by the body temperature of 37°C) = 0.0626g, and 0.0626g/2.016 (molecular weight of hydrogen) × 22.4L (mol volume) × 273 ÷ 29/273 (volume corrected by temperature) = 0.746L = 746mL, and 746mL × 75.4% (maximum hydrogen gas partial pressure at actual breathing time) = 562mL (volume at 20°C).

Estimated Hydrogen Gas Dissolving Amount in Body Fluid of the Human Body

Calculation at the time of breathing a mixed gas of H2 = 79% and O2 = 21%
Calculated supposing that the amount of breathing is 6.5L/min and the amount of blood current is 5L/min.
Calculation of hydrogen partial pressure inside the alveoli: 760Torr − 47Torr (saturated water vapor partial pressure) − 100Torr (oxygen partial pressure) − 40 (carbon dioxide partial pressure) = 573Torr/760Torr = 0.754 (hydrogen gas partial pressure)
Estimated value of dissolution (per minute) into arterial blood = 5L/min (amount of blood current) × 0.5 (water content ratio in blood) × 0.00162g/L (dissolved amount of hydrogen at 20°C) × 0.92 (corrected temperature value by body temperature) × 0.754 = 0.00281 g/min; therefore, about 33.5mL/min is absorbed and dissolved at 20°C.
Hydrogen gas consumption per minute = 6.5L/min × 0.79 = 5.135L/min
0.0335 ÷ 5.135 = 0.00652 = 0.652%

Estimated Maximum Intake Amount per minute at the time of
Hydrogen-Rich Mixed Gas Breathing
(Dissolved Amount in Blood and Efficiency)

FIG. 11

Safe Releasing System of Breathing Air to
Atmospheric Air

FIG. 12

Safe Releasing System of Breathing Air to Atmospheric Air

Charged micro-particle water

FIG. 15

Detonation flame arrester made of porous metal fibers
(to be assembled into device)

FIG. 16

HYDROGEN-RICH GAS MIXTURE BREATHING SYSTEM

TECHNICAL FIELD OF THE INVENTION

The present invention relates to a breathing device or such a system for mixing a hydrogen gas to air or oxygen to form a breathing gas for use in reducing adverse effects of active oxygen generated in the body to a human body so as to be sucked, and in particular concerns a hydrogen-mixed gas breathing system characterized by dealing with a hydrogen-mixed gas having a high concentration exceeding a hydrogen concentration of 4%, which is an unexplored field, by using the system and further additionally installing a special aerosol suction device so as to add a treatment function for various diseases such as pneumonia or the like.

BACKGROUND OF THE INVENTION

It has been known that $H_2$, that is, molecular hydrogen, has a function for selectively detoxifying a hydroxyl radical .OH of active oxygen that is harmful to the body. In recent years, by taking this function into consideration, a product formed by dissolving a hydrogen gas into water (referred to as "hydrogen water"), an article formed by dissolving a hydrogen gas in an infusion or a storage liquid for use in an infusion treatment, a suction-type device for allowing a hydrogen-mixed gas to be directly taken into the alveoli through breathing, etc. have been utilized.

Among these, with respect the suction-type device for a hydrogen gas, animal experiments or clinical trials have been carried out by using a mixed gas having a hydrogen concentration of less than 4% so that a superior effect for selectively eliminating a hydroxy radical having the highest oxidizing strength of active oxygen generated in the body has been found out. In this case, however, the value of the hydrogen concentration of 4% or less is determined so as to avoid the following ranges from the safety point of view, since with respect to an explosion-hazard range of a hydrogen-mixed gas, an explosion or a combustion tends to occur as a mixed gas when a catching fire point (igniting point) is located between a lower-limit mixed gas ratio of 4.1% and an upper-limit mixed gas ratio of 74.2% in the case of a mixed gas between air and hydrogen, as well as between a lower-limit mixed gas ratio of 4.65% and a higher-limit mixed gas ratio of 93.3% in the case of a mixed gas between oxygen and hydrogen.

Therefore, various suction tests using a hydrogen-mixed gas having a hydrogen gas concentration of less than 4% are carried out in accordance with a disaster-prevention safety standard for preventing an explosion-combustion accident in the industrial field centered on the energy field, and its concentration is not necessarily an optimal value in the human body, and there are still unexplored fields left in the aspects of animal experiments, clinical tests or actual treatments and preventions of various diseases so as to confirm the possibility of various functional effects by the application of a hydrogen-mixed gas exceeding the concentration of 4%, and this implicit limitation of 4% or less has caused one reason of intervening the progress of medicine.

Moreover, in the case of a device disclosed by JP-A No. 2009-5881 that is supposed to desirably set the hydrogen gas concentration to be sucked, the device fails to ensure an oxygen partial pressure of 21% in concentration required for daily breathing of a human body, and if the hydrogen concentration is set to 30% in the device of JP-A No. 2009-5881, oxygen needs to be obtained from the rest of 70% of air, with the result that the total oxygen concentration becomes an oxygen concentration of about 14.7%, which is lower than the lower limit value of an oxygen concentration required for the human body or lower than the lower limit value of the safety standard of 18%, causing suffocation due to lack of oxygen. Moreover, no safety measures have been taken into consideration against the fact that the explosion lower limit concentration of hydrogen gas is exceeded, with the result that if a discharge is generated in the periphery of the corresponding portion due to static electricity or the like, there is a risk of an explosion-combustion accident; therefore, the device of JP-A No. 2009-5881 is considered to be unfinished as a practical device.

Furthermore, another method has been utilized in which as one of folk remedies, a mixed gas having 66% of hydrogen and 33% of oxygen obtained by electrolyzing water is sucked from nostrils by using a cannula; however, the hydrogen gas concentration of 66% corresponds to a concentration inside the introduction tube from a supply side to the nostril cannula, with the result that the hydrogen gas is actually mixed with ambient air so that the hydrogen gas actually sucked from the nostrils into the bronchi has a hydrogen gas concentration of 4% or less, and on the assumption from its flowing rate, the hydrogen gas concentration is normally less than 1% in most cases.

Furthermore, most of suction treatments and treatment tests of a hydrogen-mixed gas currently put into practice are assumed to be applied to a person having a nearly normal lung function, and for example, persons having diseases, such as viral pneumonia, bacterial pneumonia or the like, are out of the subject, and as the suction treatment, no method other than the sole use of a hydrogen-mixed gas has been assumed.

CITATION LIST

Patent Literature

PTC1: JP-A No. 2009-5881
PTC2: Japanese Patent No. 5106110

Non-Patent Literature

Non-Patent Literature 1: "Anti-oxidant Treatment Method and Preventive Medicine of New Concept using Hydrogen Molecules" Experimental Medicine published by (Yodosha) Vol. 26, No. 13, pages 2074 to 2080, August Issue in 2008, written by Shigeo Ohta and Ikuro Ohsawa

SUMMARY OF THE INVENTION

Technical Problem

A first object to be achieved by the present invention is to provide a safe hydrogen-rich gas mixture breathing device and such a system in which with respect to a hydrogen-mixed gas breathing system using a hydrogen gas referred to as having a minimum igniting energy of 0.019 mJ (milli-Joule) is used, while on the other hand, air or oxygen or a mixed gas of air and oxygen is used, a mixed gas having a concentration exceeding an explosion lower-limit concentration (mixed ratio) of hydrogen is freely adjusted in its hydrogen gas concentration, while ensuring an oxygen concentration required for the human body and preventing an explosion-combustion damaging accident or the like (human-body damages or the like) by using a multiplex safe defensive system.

With respect to a second object, it has been found that in the case when a human being inhales a hydrogen mixed gas, upon assumption (calculation) that how much hydrogen gas is actually absorbed in the blood of the human body by breathing, 99% or more of hydrogen gas component (amount) that has been sucked (inhaled) is discharged as breathing air, without being absorbed in the human body, based upon the physiological characteristics relating to the breathing organs and circulation organs. Therefore, the second object of the present invention is to provide a safe treatment method (system) for this breathing air having a combustion-explosion characteristic and a system for improving the utilization efficiency of the hydrogen gas.

With respect to a third object, although it has been indicated that the suction of a hydrogen-mixed gas is effectively used for eliminating a hydroxy radical of active hydrogen relating to an inflammatory effect generated inside the body, by applying, in contrast, hydroxy radical or a substance having a similar function not only to a person having healthy lung functions, but also to a patient suffering from viral or bacterial pneumonia or the like in a limited manner so as to stop the advance of the disease, the oxidation actions respectively possessed and the reduction action possessed by the hydrogen gas are controlled in a well-balanced manner so as to be reacted on the alveoli surface or the like so that a redox control (oxidation-reduction control) on the alveoli surface; thus, it is possible to provide a hydrogen-rich gas mixture breathing device and such a system by which virus or bacteria adhered to the alveoli surface are partially annihilated or reduced to consequently to alleviate the disease.

Solution to Problem

In order to deal with a mixed gas having a concentration exceeding an explosion lower-limit concentration (mixing ratio) of hydrogen, prevent explosion-combustion damaging accidents or the like (human body damages or the like) and configure a multiplex safe defensive system, in all the routes made in contact with a hydrogen mixed gas, the constituent elements are formed by using an intrinsically safe structure against the explosion-hazard range of the hydrogen-mixed gas. Moreover, the first characteristic of the invention is to install a means which, if a combustion flame or a detonation state should occur in the middle of a route, would block the propagation of the flame or detonation wave in the mid-way, such as, for example, a detonation flame arrester or a water bubble-type flame intercepting device or the like, so that breathing organs of a human body are protected.

Next, as a safe treatment method (system) for breathing air having a combustive or explosive property, the breathing air having the combustive or explosive property, as it is, is subjected to a combustion process by using a small-size engine or the like so as not to cause a back fire, or diluted and mixed with air in a safe manner so as to be discharged into the air with a safe concentration.

Moreover, as the second characteristic, in order to improve the utilization efficiency of the hydrogen gas, a circulation-type breathing system is configured in which, by carrying out a reducing process, removing process or the like, on carbon dioxide in the breathing air by using an absorbent, and by further adding to this an oxygen gas or a hydrogen gas so as to be utilized as a rebreathing gas.

Furthermore, with respect to a patient suffering from viral or bacterial pneumonia or the like, a means is additionally used, in a separated manner from a supply line for the hydrogen-rich mixed gas, in which aerosol mainly composed of charged micro-particle water in which hydroxyl radical, that is, .OH, is dissolved or contained is sprayed and supplied, and suction of the aerosol and suction of the hydrogen-rich gas mixture are switched in a desired timing so as to provide a usable gas route connection, or by carrying out an action having the same effect as described above, the aerosol is allowed to reach the inside of the alveoli of the user so that virus or bacteria adhered to the surface of the alveoli are partially annihilated or reduced to consequently to alleviate the disease, which forms the third characteristic of the invention.

In this case, in place of the charged micro-particle water in which a hydroxyl radical, that is, .OH, is dissolved or contained, by using aerosol mainly composed of micro-droplets or micro-particle water in which an ascorbic acid complex relative to at least divalent iron ion $Fe^{2+}$ or monovalent copper ion $Cu^+$ of transition metal ions is dissolved or contained, such a function is exerted in which by the Fenton reaction in which the divalent iron ion $Fe^{2+}$ or monovalent copper ion $Cu^{+2}$ that has reached the inside of the alveoli reacts with hydrogen peroxide generated by an immunoreaction such as microphages or the like caused by pneumonia or the like, a hydroxy radical or .OH is generated on its surface so that virus or bacteria is partially annihilated or reduced to consequently to alleviate the disease. Moreover, these metal ions cause the repetitive Fenton reaction by the Haber-Weiss reaction due to superoxide anion $.O_2^-$ caused by an immunizing-function or the like so as to function like a catalyst.

With respect to the switching between the suction of aerosol and the suction of a hydrogen-rich mixed gas, in the case of the aerosol mainly composed of charged micro-particle water, although no residual effect (residual effectiveness) after the stoppage is exerted, the breathing air that contains a hydrogen gas having a high concentration is not directly discharged to the atmospheric air, but always subjected to a treatment by a safe means to be divided into aerosol and air with a low concentration, that is, a hydrogen concentration of 4% or less, and discharged, while in the case of breathing air containing a hydrogen gas within a concentration of 4%, it may be directly discharged into the air. Alternatively, in the case when the aerosol, mainly composed of micro-droplets or micro-particle water in which an ascorbic acid complex relative to divalent iron ion $Fe^{2+}$ or monovalent copper ion $Cu^+$ is dissolved, is used, a residual effect (residual effectiveness) is exerted to cause a catalytic function; therefore, this point needs to be taken into consideration.

Furthermore, in the case when such aerosol is used, after the hydrogen gas concentration has been reduced to a regulated concentration or less, while a safety maintenance is ensured during a gas exchange of the hydrogen-rich mixed gas occupied in the total lung capacity (TLC) including the inside of the alveoli in the previous process, switching of the suction is carried out to the aerosol suction (breathing) process.

Alternatively, in this process, since the aerosol is transferred by using normal air, in order to next carry out a process for allowing the suction (breathing) of the hydrogen-rich mixed gas, a scavenging process by the use of an oxygen gas is required so as to discharge and reduce a nitrogen gas occupied in the total lung capacity (TLC) including the inside of the alveoli. Moreover, in the case when the nitrogen gas concentration becomes a set value (desired value) or less by the scavenging process, the sequence proceeds to a forceful circulation process by the use of a hydrogen-rich mixed gas. Furthermore, with respect to the generation method of aerosol, since there are some methods, such as a pressurizing system, an ultrasonic wave system, an electrostatic system or the like, as an atomizing method, one of these may be adopted depending on the situation.

Moreover, since the present treatment method using aerosol is an extremely special method, it is of course carried out under complete managements and continuous diagnoses by a plurality of medical specialists and related specialized technicians. Since one portion of the ingredient of aerosol might be directly taken into a vein, that is, into blood from the alveoli, regarding to this point, as well as regarding to the administration dosage, strictly controlled processes need to be carried out. In the case of using transition metal ions, after the treatment, post treatments using a safe metal chelate agent, such as suction by aerosol or administration through mouth or intravenous infusion or the like thereof, are carried out, if necessary.

Effects of Invention

Figure 11:
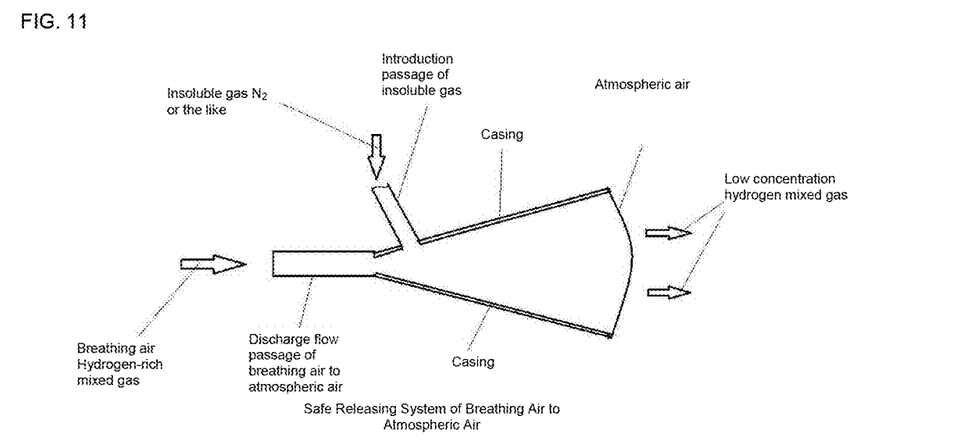
FIG. 11 is an explanatory view showing a safe releasing system of breathing air into the atmospheric air.
Figure 12:
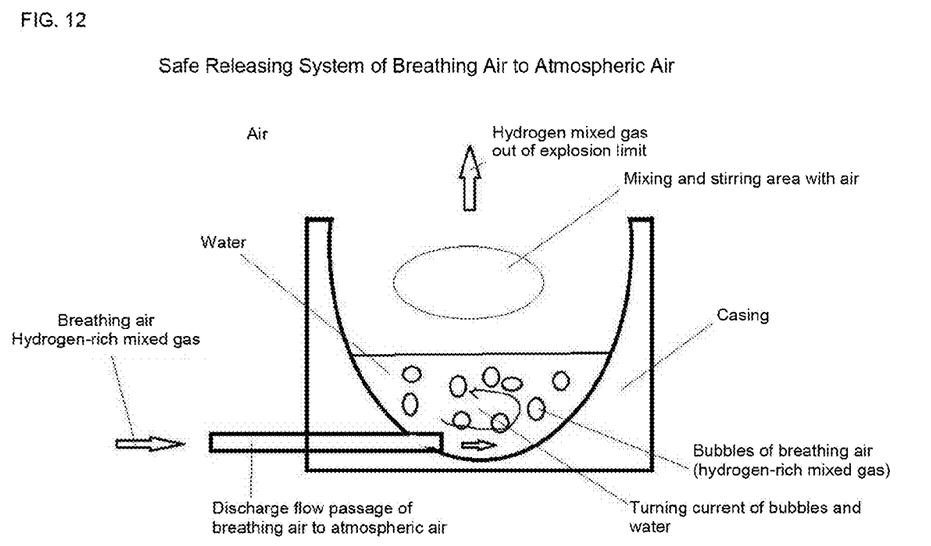
FIG. 12 is an explanatory view showing a safe releasing system (water bubble type) of breathing air into the atmospheric air.

The hydrogen-rich gas mixture breathing system of the present invention, which has its device main constituent elements made of an intrinsically safe explosion-preventive structure, makes it possible to prevent the possibility of ignition due to a frictional energy or an electrostatic discharge that causes an explosion/detonation of a hydrogen-rich mixed gas, and by further safely treating breathing air by using a device shown in FIG. 11 and FIG. 12, shown in Table 1, it becomes possible to suck such a mixed gas, having a concentration ranging from the lower explosion limit to the upper explosion limit of a hydrogen mixed gas. In the present invention, even in the case when a fire occurs in the device in case of contingency, since a breathing-use detonation flame arrester or a water bubble-type flame intercepting device is installed on the periphery or an appropriate place of the breathing mask, it is possible to provide a basic system for allowing the hydrogen-rich mixed gas to be sucked safely.

Figure 9:
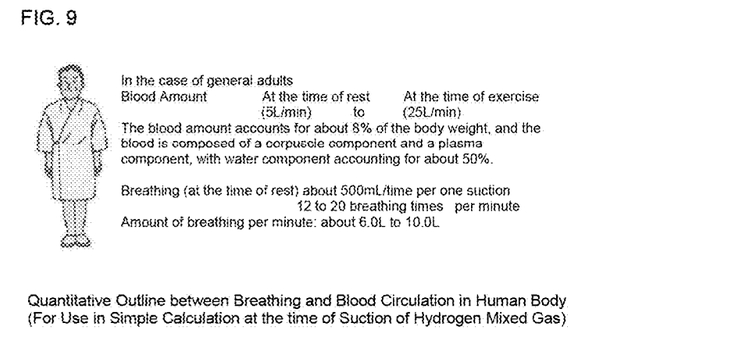
FIG. 9 is an explanatory view showing a quantitative outline of the breathing and blood circulation of the human body.
Figure 10:
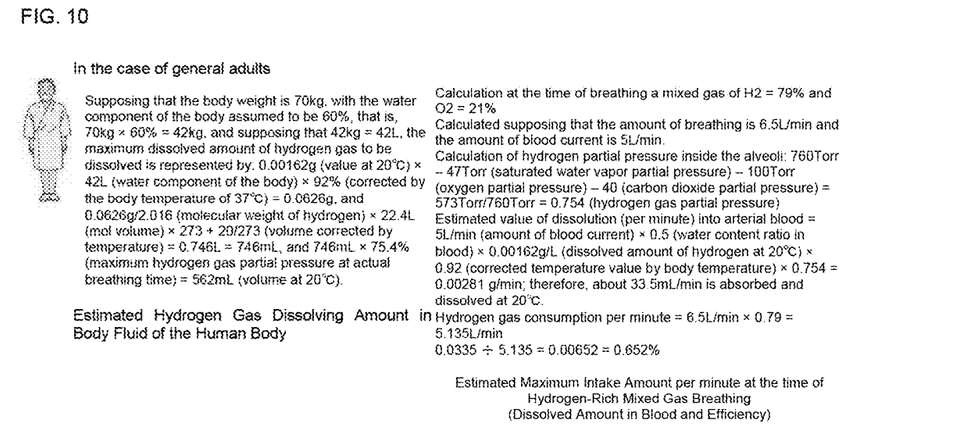
FIG. 10 is an explanatory view showing an estimated hydrogen gas dissolved amount in body fluid in a human and an estimated maximum intake amount per minute at the time of breathing a hydrogen-rich mixed gas.

Secondly, with respect to the utilization efficiency of hydrogen gas, FIG. 9 is an explanatory view showing a quantitative outline in general between the breathing and blood circulation in the human body. Moreover, FIG. 10 is an explanatory view indicating an estimated amount of hydrogen gas dissolved amount in the body fluid of the human body in the case when nitrogen gas in the air (=79%) is replaced (substituted) by hydrogen gas and an estimated value of the maximum intake amount (intake dissolved amount in blood) in the human body (in blood) per minute in the case when the gas of this concentration is breathed. Additionally, the calculation is carried out supposing that the hydrogen gas is dissolved in a water portion of a plasma component of the blood. For example, in the case of a person having 70 kg in weight, even when hydrogen gas is dissolved in all the water component in the body fluid through breathing, the amount is as small as about 0.56 L, and the intake amount in blood per minute through breathing is about 33.5 mL/minute. The efficiency relative to sucked hydrogen gas at that time is about 0.65% (in the present calculation, a returning portion to the vein side is ignored).

Therefore, in this case, a circulation-type breathing passage is formed, and carbon dioxide in breathing air is absorbed (adsorbed) by using a canister or the like, and an oxygen gas is added thereto, while a hydrogen gas is added thereto, if necessary. The system of the present invention makes it possible not only to greatly increase the utilization efficiency of hydrogen gas, but also to greatly contribute to the safety point of view by refraining from using unnecessary hydrogen gas and oxygen gas (the required amount of hydrogen gas is reduced to about one several hundredth by adopting the circulation type). Table 2 shows one example in comparison with another method for taking a hydrogen gas in the same manner. The table shows intake means for hydrogen gas and a simple calculation estimated value of dissolved amount in blood. In the case when a hydrogen gas is taken in through breathing, the hydrogen gas concentrations are approximately calculated to 33.5 mL/minute when $H_2=79\%$ and 1.67 mL/minute when $H_2=4\%$, and in the case when 1 L of hydrogen water is drunk simultaneously, the concentration is calculated in the same manner as 7.2 mL/L (supposing that the absorbing rate is 40%), while in the case when the hydrogen water is taken through a venous infusion simultaneously, the concentration is approximately calculated as 18 mL/L. Therefore, with respect to the hydrogen gas intake amount per minute, the system of the present invention exerts the maximum capability. (Although the calculations are approximate ones, there is no error in its tendency.)

Figure 13:
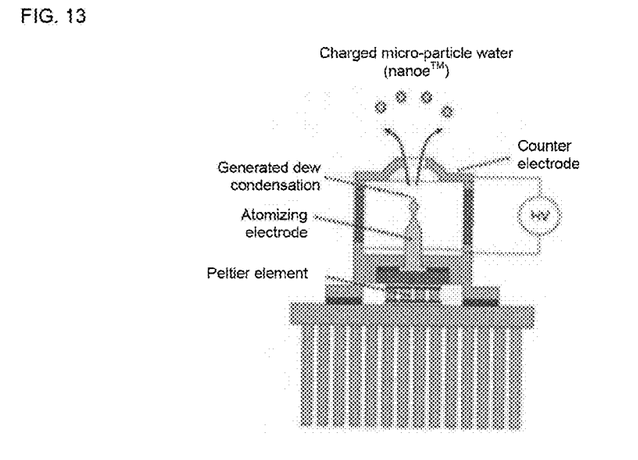
FIG. 13 is a schematic view (substituted by photograph) of a generation device for charged micro-particle water (nano ion$^-$)
Figure 14:
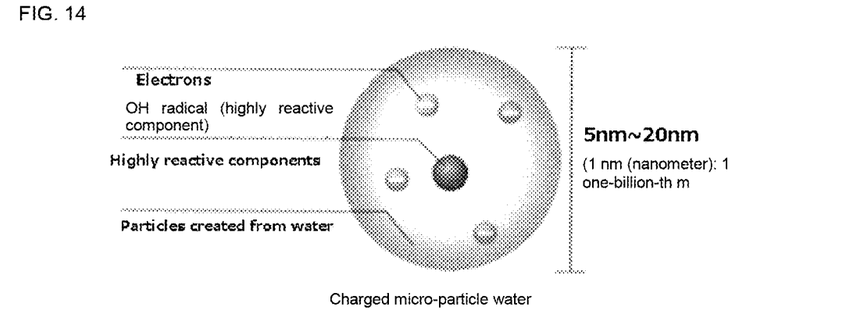
FIG. 14 is an explanatory view showing a state of charged micro-particle water (substituted by photograph)
Figure 15:
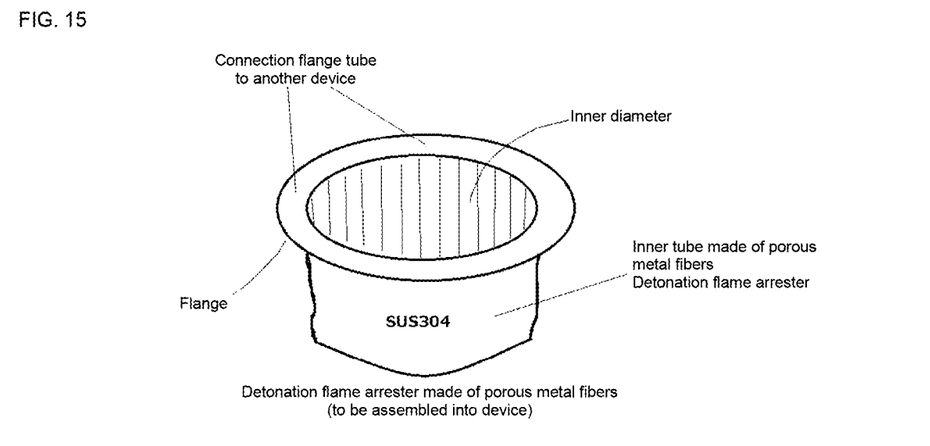
FIG. 15 is an explanatory view showing a detonation flame arrester made of porous metal fibers (to be assembled in an apparatus) (embodiment 4)
Figure 16:
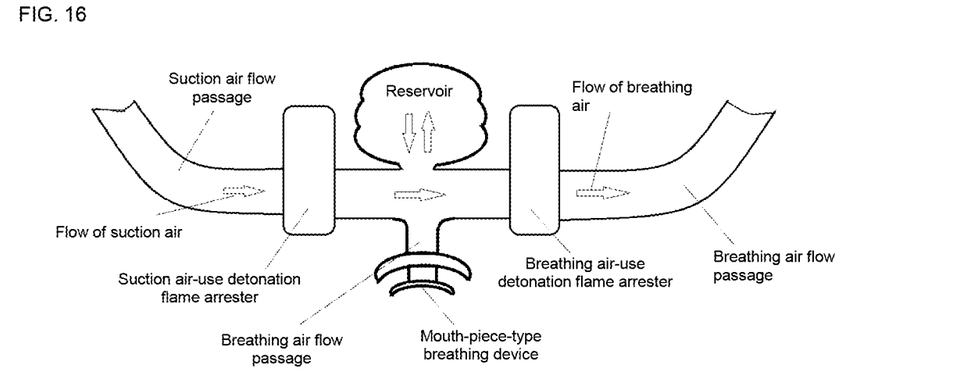
FIG. 16 is an explanatory view showing a mask portion of a forced circulation type hydrogen-rich gas mixture breathing system using a mouth-piece-type breathing device.

Thirdly, with respect to a special method for patients suffering from SARS virus (Severe Acute Respiratory Syndrome (SARS in abbreviation)) or bacterial pneumonia, the SARS virus thinly propagates on the alveoli surface in accordance with a certain diagnosis and treatment record. Moreover, in the recent bacterial pneumonia, the bacteria have come to exert a resistant against antibiotics so that no effects are obtained in many cases. In view of these circumstances, for example, by utilizing a charged micro-particle water generator as shown in FIG. 13 developed by Japanese Panasonic Corporation or the like, charged micro-particle water as shown in FIG. 14 is generated, and by allowing this to be sucked by the corresponding patient as aerosol together with air, SARA virus adhered and propagated on the alveoli surface can be reduced or eliminated by the effect of OH radical (hydroxy radical) contained in the charged micro-particle water. Moreover, it has been proved that the hydroxy radical is effectively used for depriving almost all the virus and bacteria of their vitality, by exposure tests carried out within a narrow space by the enterprises. Moreover, it has also been known that when made in contact with hydroxy radical, the hydrogen gas makes it chemically reacted and finally changed into harmless water. Therefore, by utilizing the oxidation reaction possessed by hydroxy radical and the reduction reaction possessed by hydrogen gas, the present invention provides a system capable of decomposing and removing an applied portion of excessive hydroxy radical through suctions of a hydrogen-rich mixed gas carried out before and after the application process.

Moreover, in the case when in place of charged micro-particle water, an aerosol mainly composed of micro-droplets or micro-particle water in which divalent iron ion $Fe^{2+}$ or monovalent copper ion $Cu^+$ and an ascorbic acid complex are dissolved is used, it has been reported that in the case of using, for example, divalent iron ion $Fe^{2+}$ and an ascorbic acid complex, the sterilizing strength is increased to 100 times to 2000 times in comparison with the ascorbic acid (Agricultural Department of Saga University). By sucking the ascorbic acid complex having such a strong oxidizing capability together with suction air as an aerosol, it is deposited on the alveoli surface contaminated by virus or the like, and during a period in which an excessive ascorbic acid is oxidized, hydrogen peroxide is generated, with hydrogen peroxide being further generated by an immunizing function, to cause the Fenton reaction between it and the corresponding metal ion, with the result that a hydroxy radical is generated to annihilate or sterilize the virus or the like on the contact surface and the divalent iron ion $Fe^{2+}$ is changed to trivalent iron ion $Fe^{3+}$, and further changed to divalent iron ion $Fe^{2+}$ by superoxide anion $.O_2^-$ caused by an immunizing-function (Haber-Weiss reaction) so that the repetitive Fenton reaction is carried out. Moreover, the iron ion or copper ion is partially taken into blood directly inside the vein through the alveoli. The present invention provides a system in which suction processes of a hydrogen-rich mixed gas are prepared before and after the above-mentioned process so that hydrogen gas dissolved and remained in the blood makes it possible to greatly reduce and eliminate the Fenton reaction in the blood or other cells or organs, that is, the generation of hydroxy radical.

TABLE 1

| | Explosion Lower limit (%) | Detonation Lower limit (%) | Detonation Upper limit (%) | Explosion Upper limit (%) | |
|---|---|---|---|---|---|
| Hydrogen-Air Mixture | 4.1% | 18.3% | 59.0% | 75.0% | Hydrogen gas temperature |
| | 20.1% | 17.2% | 8.6% | 5.3% | Oxygen gas temperature |
| | 75.8% | 64.5% | 32.4% | 19.7% | Nitrogen gas temperature |
| Hydrogen-Oxygen Mixture | 4.7% | Unknown | Unknown | 93.3% | Hydrogen gas temperature |
| | 95.3% | | | 6.7% | Oxygen gas temperature |

Low ⟹ High
Hydrogen gas concentration
Explosion Range of Hydrogen Gas and Characteristic of Detonation Wave Range
(Hydrogen on the upper side, oxygen on the lower side)

TABLE 2

| Using Means | Contents of Administration | Estimated Dissolving |
|---|---|---|
| Suction of Gas | $H_2$ = 79%, $O_2$ = 21% | 33.5 mL/min |
| Suction of Gas | $H_2$ = 4%, $O_2$ = 21%, $N_2$ = 75% | 1.67 mL/min |
| Hydrogen Water | 20° C., 1.62 ppm, concentration | 7.2 mUL |
| Intravenous Infusion | Intravenous infusion at hydrogen | 18 mUL |

Hydrogen Gas Intake Means and Simple Calculation Estimated Value of Dissolved Amount in Blood

DESCRIPTIONS OF THE PREFERRED EMBODIMENTS

A hydrogen-rich gas mixture breathing system is realized in which a suction device of a hydrogen-rich mixed gas is formed by using an intrinsically explosion-preventive structure in which by suppressing the occurrence of frictional heat or static electricity centered on the contact surface between the device and hydrogen gas, generation of a minimum igniting energy of hydrogen gas is prevented, and by further adopting a detonation flame arrester or a water bubble-type flame intercepting device, a duplicated preparation for the occurrence of an unexpected explosion-detonation of hydrogen gas is made, and by also preparing a safe releasing system to the air of breathing air containing a hydrogen-rich mixed gas so that by adopting a circulation-type breathing system in which carbon dioxide in components of breathing air is absorbed and a re-breathing process is carried out by adding an oxygen gas or a hydrogen gas thereto, as well as by adopting an aerosol generation device using charged micro-particle water (nano ion$^-$) in which hydroxy radical having a high oxidizing strength is dissolved (contained) is operated in combination or an aerosol generation device using micro-droplets or micro-particle water having divalent iron ion $Fe^{2+}$ or monovalent copper ion $Cu^{+2}$ capable of exerting a similar function as main components to be used in combination; thus, by using these devices together with a managing and executing technique for ensuring safety on the periphery, it becomes possible to highly ensure safety.

EXAMPLES

Figure 1:
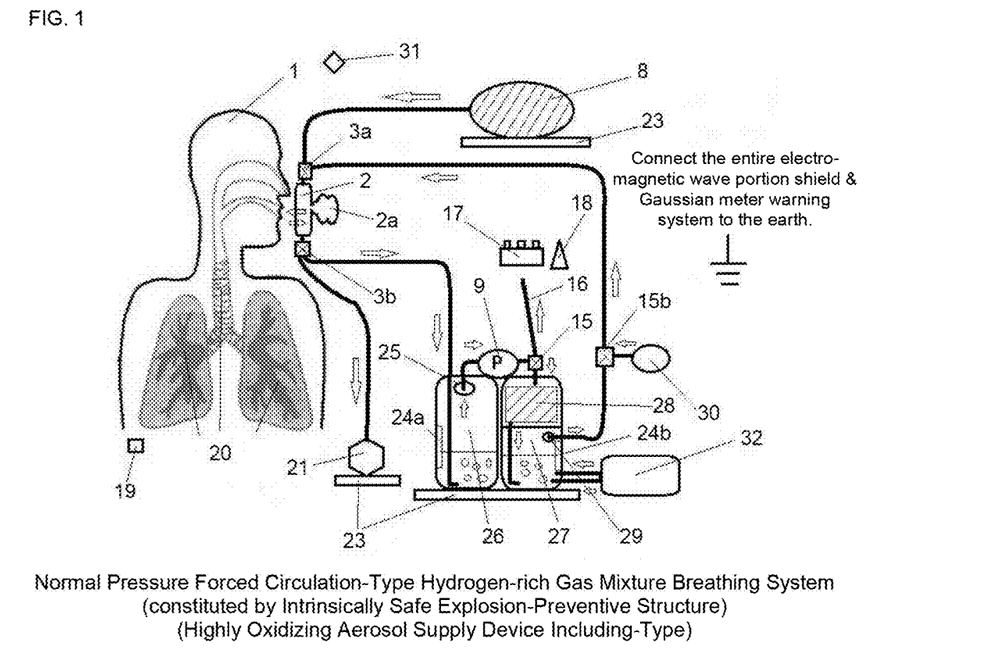
FIG. 1 is an explanatory view showing a hydrogen-rich gas mixture breathing system of a normal-pressure forced circulation type (with a water bubble-type flame intercepting device and an aerosol supply device installed in combination) (embodiment 1)
Figure 2:
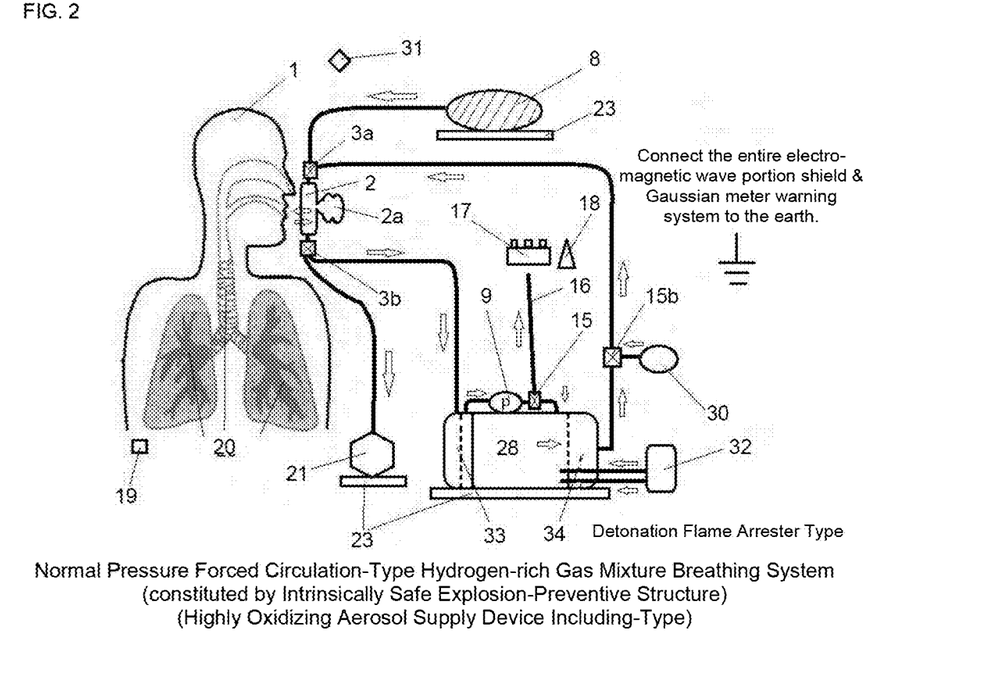
FIG. 2 is an explanatory view showing a hydrogen-rich gas mixture breathing system of a normal-pressure forced circulation type (detonation flame arrester type) (embodiment 2)
Figure 3:
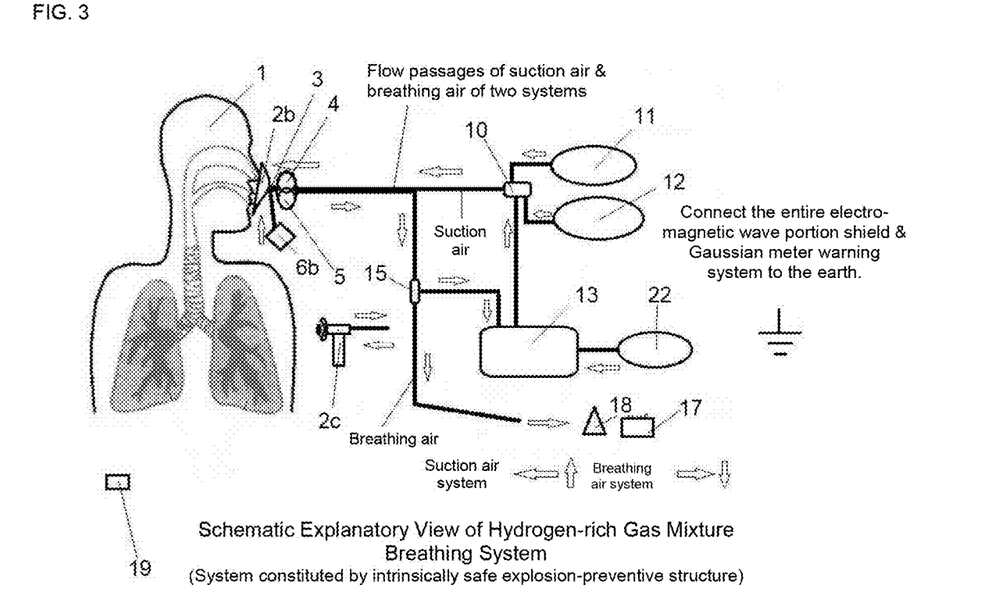
FIG. 3 is a schematic view of the hydrogen-rich gas mixture breathing system (non-forced circulation type) (embodiment 3)
Figure 4:
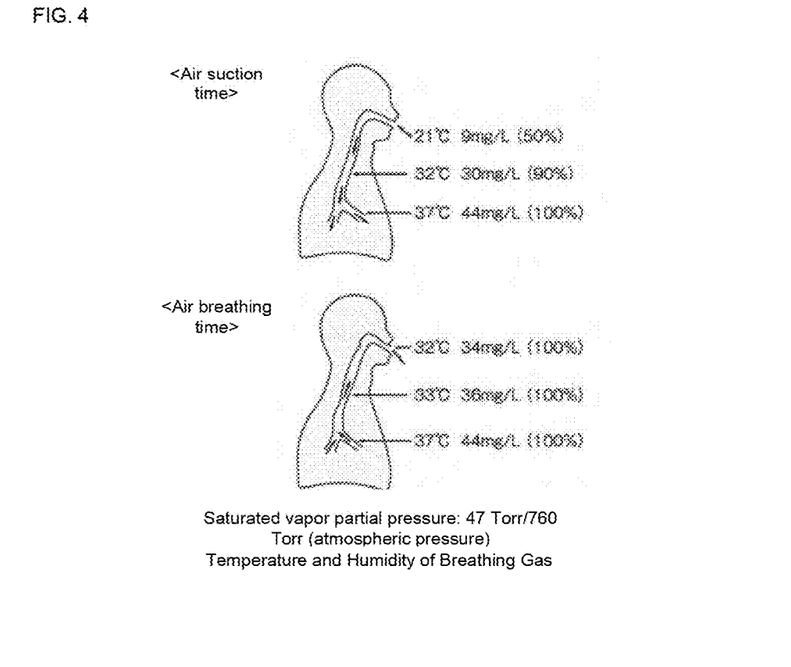
FIG. 4 is an explanatory view showing the gas temperature and humidity in breathing of a human body.
Figure 5:
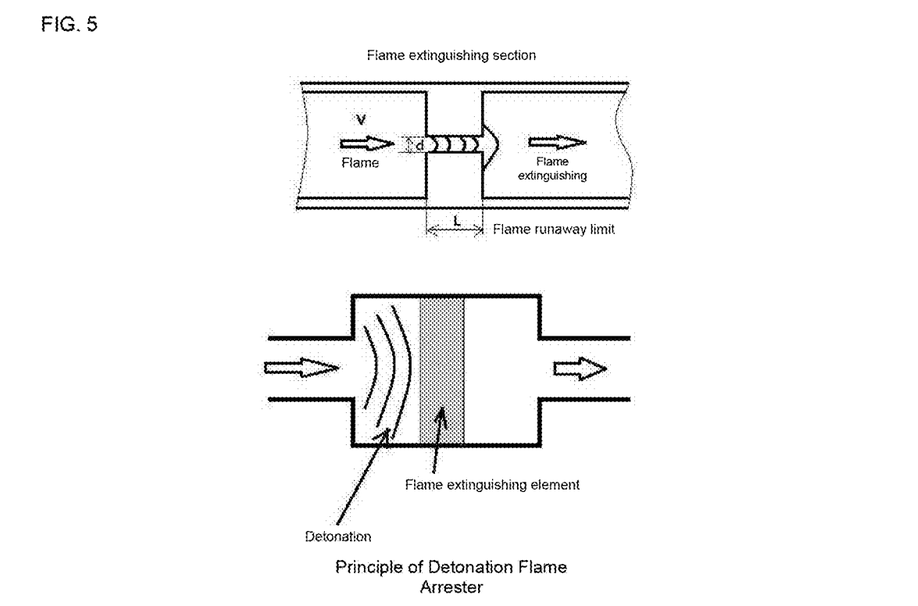
FIG. 5 is an explanatory view showing operations (principle) of the detonation flame arrester.
Figure 6:
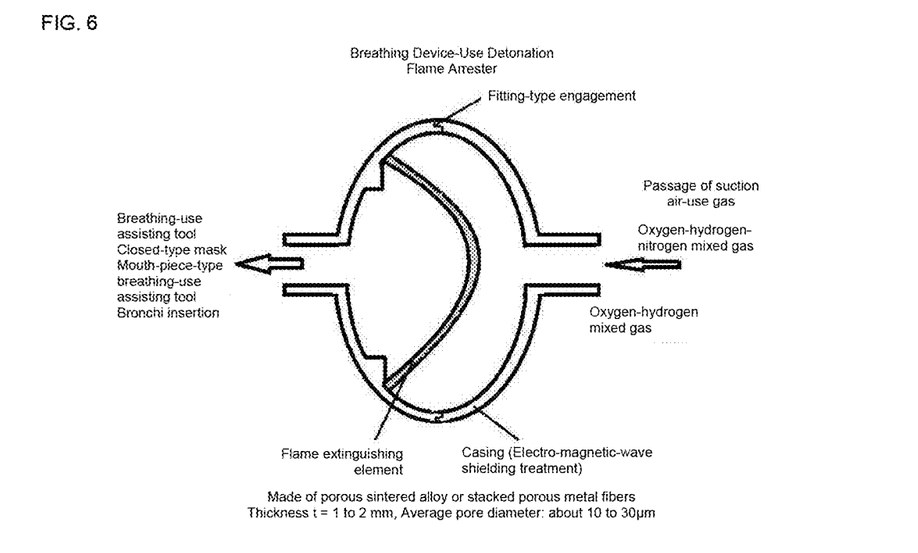
FIG. 6 is an explanatory view showing the detonation flame arrester for a breathing device.
Figure 7:
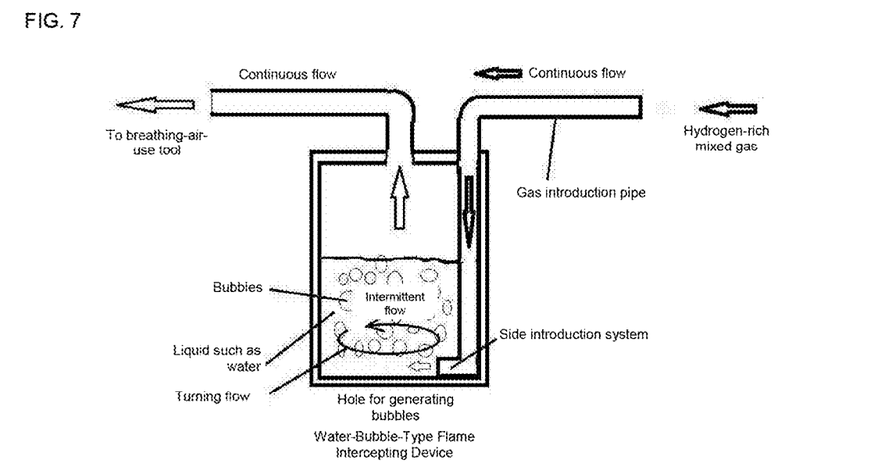
FIG. 7 is an explanatory view showing a water bubble type flame intercepting device.
Figure 8:
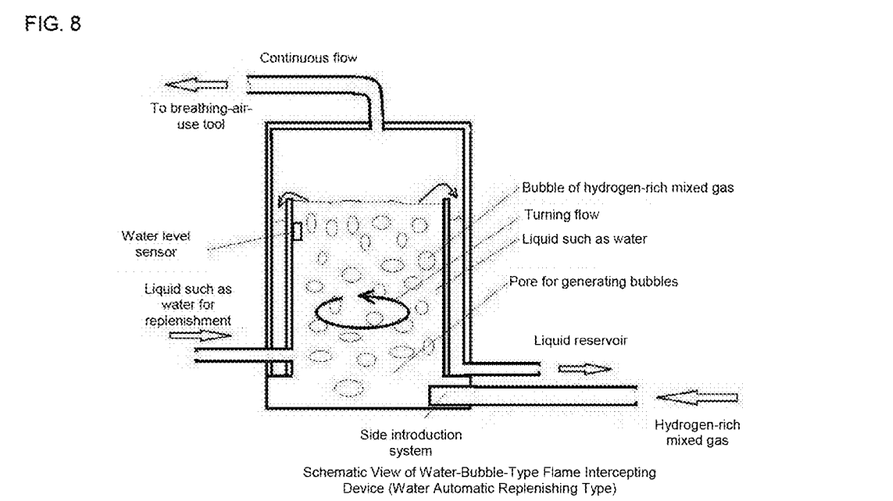
FIG. 8 shows a water bubble type flame intercepting device (water automatic supply type)

FIG. 1 is an explanatory view, which shows a first example of the present invention, is the same as the configuration of FIG. 2, with the only difference lying in whether a water bubble-type flame intercepting device or a detonation flame arrester is used. In this case, what is important is that the safety of the present system to be ensured is half occupied by the safety of the present device and system, and the rest half is occupied by the working procedure on usage and ambient safe environment management. Consequently, since a trivial corner-cutting or carelessness might lead a serious accident, in particular, the operation having an increased hydrogen mixed gas concentration should be carried out by expert personnel (for example, an expert for hydrogen-gas disaster prevention, an expert doctor, etc.) under special management. Moreover, with respect to the safety issue on the human body side, as shown in FIG. 4, the relative humidity from the inside of an oral cavity to the respiratory tract and the alveoli is set to nearly 100% so that there are no case examples about an igniting phenomenon, a discharging phenomenon, or the like inside the human body. Moreover, with respect to teeth of the human body, although there are some matters, such as false teeth made of metal or the like, to be concerned, these are matters to be individually dealt with (as an electromagnetic energy interference with the outside). Furthermore, with respect to a person with a pacemaker attached therein or a person with medical equipment having an energy source embedded therein, or the like, these cases are to be individually dealt with.

In FIG. 1, in the case when the treatment is carried out indoors, the humidity management is appropriately carried out in order to prevent an electrostatic explosion, and the standard humidity is set to approximately 60%. In the case when air is partially used as a suction air to be breathed, after dust or the like has been removed by a filter, the resulting air is used for breathing. In order to form an intrinsically safe structure, a passage or the like with which the hydrogen-rich mixed gas is made in contact is made of a conductive material, that is, a conductor, or is subjected to a surface treatment so that all the parts and a human body are bonded (grounded). The user and the administrator, of course, put on static eliminating garments and articles, such as a mobile telephone or the like, which generate electromagnetic waves, are not permitted to be brought into the working atmosphere. With respect to movable portions of the device also, the generated energy from those portions is set to a standard value or less. With respect to important portions (portions that are influenced by electromagnetic waves and hazardous), the outside (outside surface) thereof is coated with an electromagnetic wave shielding agent or the like. If necessary, a Gaussian meter or the like for use in electromagnetic wave detection or warning is installed.

First, the target hydrogen concentration of a hydrogen-rich mixed gas is determined. Next, the operation time is determined. From the standard viewpoint of the present device, the operation time of one hour or less is assumed (since this is determined for making an appropriate effect judgment, not less than this period of time may be used.)

1) In a suction process of the hydrogen-rich mixed gas, a closed breathing mask 2 is attached to the user (that of a mouth-piece type may be used).

Next, by setting a switching valve 15*b* to a 30 side, air is supplied to the 2 side. At this time, a valve 3*b* is set to a circulation side of 26. Simultaneously, a suction pressure applying pump 9 is operated. Moreover, a switching valve 15 is set to a non-circulation externally releasing passage 16 side. This is a test operation using normal air so as to confirm whether or not a normal air flow is obtained, whether or not the attached state of the mask 2 is appropriate and whether or not the breathing is easily carried out. Moreover, checks are made as to whether or not any problem is raised in a reservoir 2*a*, whether or not the pressure setting is correct, and the like.

When no problems are raised in the processes so far, the sequence proceeds to the suction process of a hydrogen-rich mixed gas, and 30 is then stopped and the switching valve 15*b* is switched to the circulation side. First, only an oxygen gas is supplied from a hydrogen-gas & oxygen gas supply device at a set amount. The gas supply amount is normally set from 6 L/min to 12 L/min. At this time, if the carbon dioxide absorption of the circulation type is not selected, a hydrogen gas is next supplied from 32, and the oxygen gas and the hydrogen gas are adjusted based upon set ratios so that the total amount of these at about 6 L/min to 12 L/min is supplied; thus, breathing air is directed to the flow passage 16 via a valve 15, and then subjected to a combustion treatment of 17 or released to the atmospheric air through 18 so as to be safely treated.

In the case when the circulation operation is selected, when, after carrying out the operation for a while, the nitrogen gas concentration of the breathing air and the concentration of the line are lowered to set values, the oxygen concentration at this time becomes higher than that in the normal air; therefore, by once stopping the supply of the oxygen gas, only the hydrogen gas is supplied from 32. At this time, the circulation & exhaust switching valve 15 is switched to the circulation side. In the circulation type, the supply amount of the hydrogen gas from 32 is determined as a ratio relative to the total amount. In this case, supposing that an added amount of the total lung capacity (TLC) of the user and the gas volume (space capacity) from the breathing mask 2 to the inside of the circulation line is the total amount, for example, if it corresponds to a volume of 12 L, by setting the initial hydrogen gas concentration to 30%, 12 L×30%=3.6 L so that 3.6 L of hydrogen gas in total is supplied from 32. When the oxygen concentration in the circulation passage is lowered to a set value, for example, 21%, the amount corresponding to an oxygen portion consumed by breathing is again continuously supplied from 32. During this period, the user continuously keeps breathing to take the hydrogen gas into the blood from the alveoli. Then, when the set time has elapsed or when the hydrogen concentration is lowered to the set value, the sequence proceeds to a completing process.

In the completing process, an attempt is made so as to eliminate the risk. The supplies of hydrogen gas and oxygen gas of 32 are stopped, a circulation & scavenging switching valve 15*b* is switched to the scavenging side, a scavenging air blowing device is driven, air is sent to the breathing mask 2, a pump 9 is driven, and the circulation & exhaust switching valve 15 is switched to the exhaust side so that the breathing air is treated in a safe state. When the hydrogen gas concentration in the breathing air has been lowered to a set value (normally, assumed to be about 2%), the mask can be safely removed. Then, 9 and 30 are stopped, thereby completing the operation. Moreover, in the final process, the air supply amount of 30 is reduced to the same level as that of the breathing amount so that the hydrogen concentration of the breathing air makes it possible to suppress a sensor error due to dilution. Thus, the user is allowed to take off the breathing mask 2, thereby completing the process.

Moreover, in the case when YABASHI LIME (trade name) is used as the $Co_2$ absorbent of 28, since 1 L of YABASHI LIME is said to have a standard service life of about 40 hours at 6 L/min (direct breathing amount), and 28 becomes a nearly shield state when the pump is stopped (in the case of medical application), the repetitive application is available to a certain degree (the replacement time comes when the carbon dioxide concentration in the circulation passage exceeds a set value).

With respect to the suction of the aerosol, after the completion of the suction of the aforementioned hydrogen-rich mixed gas and the completion of the scavenging process, a suction-use switching valve 3a and a breathing-use switching valve 3b are simultaneously switched to the line from an aerosol supply device 8 and an aerosol moisture capturing device 21 side, and from the device 8, air containing a highly oxidizing aerosol is sent to the mask 2 at a flow rate from about 6 L/min to 12 L/min, with the breathing mask being attached. In the same manner as in the case of the above-mentioned suction of the hydrogen-rich mixed gas, a breathing method is also important for the suction of aerosol. A deep breathing to a certain degree is important in order to send the aerosol to the deep side of the alveoli. In the case of the charged micro-particle water, the particle diameter is sufficiently small, and in the case of micro-droplets of iron ion or copper ion also, those droplets whose particle size is reduced to about 1 μm in the minimum by using a Nebulizer or another atomizing device are utilized. The treatment should be carried out under managements by respective medical specialists and specialized technicians in this field. The treatment is executed while monitoring the effective section rate of aerosol or the effective arrival rate onto the inside surface of the alveoli.

In the case when the suction process of aerosol is completed, since no explosive component is contained in the breathing air, the supply of aerosol from 8 may be simply stopped. When there is not the next process, the treatment is completed by removing the breathing mask. If the suction of the hydrogen-rich mixed gas is further carried out, by switching the suction-use switching valve and breathing-use switching valve 3*a* and 3*b* to the line for use in breathing the hydrogen-rich mixed gas, the hydrogen-rich mixed gas suction process in the initial process operation is repeated. Embodiment 2 of FIG. 2 is different in that the disaster-preventive structure in the center is changed from the water bubble-type flame intercepting device to the detonation flame arrester, with the other parts being substantially the same. Moreover, in the detonation flame arrester system, the installation position of the detonation flame arrester may be set near the breathing mask, as shown in FIG. 16. However, in the system using the detonation flame arrester, a moistening means for breathing air may be added depending on circumstances. Although no description is given to the control system, in the case of the system in this level, unitary management and control processes are normally carried out by a micro-computer or the like, together with sensor information.

FIG. 3 shows embodiment 3 in which the gas circulation of a gas flow passage is basically carried out by the breathing of a user 1 himself or herself. Reference numeral 11 represents an oxygen gas supply source, which is driven by a positive pressure of about several centimeters in a water column H20 by taking into consideration the gas transmitting resistance of the flow passage. The same is true for a hydrogen gas supply source represented by reference numeral 12. In the case when a breathing air re-circulation system utilizing a $Co_2$ absorbing device indicated by reference numeral 13 is used, with respect to the supply amount of hydrogen gas, the total amount is preliminarily determined and then supplied in the same manner as in the above-mentioned method. In place of the mask 2*b*, a mouth-piece-type mask (with a breathing valve) represented by reference numeral 2*c* may be used. In FIG. 3 (with a nose clip attached), upon occurrence of any fire or explosion at the upstream on the air-suction side or the downstream side on the air-breathing side from the detonation flame arrester indicated by reference numeral 4 or 5, an impact pressure and a flame propagating the inside of the flow passage of the hydrogen-rich mixed gas are completely blocked at the portions 4, 5 of the detonation frame arrester. Of course, in place of 4, 5 thereof, the water bubble-type flame intercepting device may be used in the same manner. In this case, however, when the air-suction-use oxygen has been consumed, the oxygen concentration of the suction air is extremely lowered, with the result that in an attempt to continue the breathing, the lack of oxygen is caused; therefore, this phenomenon is detected by an ultraviolet-ray sensor or another sensor, and by switching the switching valve 3, the outside air having a standard oxygen concentration of 21% is sucked from an emergency suction-air inlet 6*b* on the suction-air side so as to maintain breathing. Since the breathing air has a higher hydrogen concentration, it is directed through the exhaust flow passage to the tool 18 via 5 so as to be diluted and released into the air, or subjected to a burning treatment in 17. These control processes are program-controlled by sensors and computers installed at respective places. Moreover, the respective component portions to be used, such as the detonation frame arrester or the like, are checked to find out any lowered states in safety performance, such as adhesion of stains like dust or the like, and if there are any of them, the service life is considered to be expired so that the corresponding part is exchanged.

FIG. 5 explains embodiment 4 which shows one example of a detonation frame arrester to be assembled into an air breathing device or a circulation-type oxygen breathing device, and normally, this is used by being mounted on the back. By assembling this in the breathing passage right before the breathing mask, the hydrogen-rich mixed gas or the like formed by adding a hydrogen gas to oxygen is sucked so that the hydrogen gas is taken into blood in the body. Of course, the existing circulation breathing system has been changed in its design required for an intrinsically safe explosion-preventive structure so as to function for protecting lung functions of the human body from an explosive fire at the time of an unexpected accident. These are not intended to be used for normal work, but intended to be used for such a severe environment as to receive irradiation of radioactive rays, in particular, gamma ray, caused by, for example, an accident or the like in an atomic power plant, so as to reduce adverse effects of active oxygen generated when the gamma ray has passed through the human body. Moreover, the external coating formed on the assembling-type detonation flame arrester is made of an electro-magnetic wave shielding agent or the like so that influences of external electro-magnetic energy irradiation are reduced. Furthermore, in place of the detonation flame arrester, a water bubble-type flame intercepting device may be used.

INDUSTRIAL APPLICABILITY

Since the entire system of a breathing device is formed based upon an intrinsically safe explosion-preventive specification, with a detonation flame arrester or the like being further installed as a safety device, the upper-limit concentration of 4% in the utilization of a hydrogen mixed gas is eliminated so that it becomes possible to step into an unexplored field, and to carry out wide-range experiments, treatment tests and practical utilizations with respect to various medical effects and applications originally possessed by the hydrogen gas. Moreover, not limited by protection against radioactive rays (to reduce active oxygen in the human body generated by a gamma ray), on the contrary, by utilizing hydroxy radical between hydrogen gas and active oxygen, this system is also applicable to an assisting process or the like for treatments relating to various viruses, multi-agent resistant bacteria or the like inside the alveoli.

EXPLANATION OF REFERENCE NUMERALS 1 human body (user of hydrogen-rich mixed gas breathing device)
2 breathing mask (closed type) (with a built-in pressure-amount sensor)
2a reservoir
2b breathing mask (with breathing valves)
2c mouth-piece type mask (with breathing valves and a nose clip attached thereto)
3 breathing passage switching valve (suction air switching)
3a suction-use switching valve
3b breathing-use switching valve
4 suction-use detonation flame arrester (made of porous metal fibers)
5 breathing-use detonation flame arrester (made of porous metal fibers)
6b inlet for emergency suction air
8 aerosol supply device (charged micro-particle water or micro-droplets or micro-particle water containing transition metal & ascorbic acid complex)
9 suction pressure applying pump (oval pump or the like)
10 switching valve
11 oxygen gas supply source
12 hydrogen gas supply source
13 $Co_2$ absorbing device (absorbent, calcium hydroxide or the like: YABASHI LIME or the like)
15 circulation & exhaust switching valve
15b circulation & scavenging switching valve
16 exhaust gas flow passage
17 device for carrying out a burning process on breathing air by using an engine or the like
18 tool or the like for safely releasing breathing air into the air
19 human body sensor (pulse oximeter, capnometer or the like)
20 portion indicating from the bronchia to the alveoli of the human body
21 aerosol moisture capturing device
22 oxygen gas supply source
23 base of the device (mount)
24a water level meter of breathing air-suction tank (including a water thermometer)
24b water level meter of suction air pressurizing tank (including a water thermometer)
25 breathing air-suction inlet and various gas sensors ($Co_2$ concentration, $H_2$ concentration, $0_2$ concentration or the like)
26 breathing air suction container (driven under negative pressure)
27 circulation gas sending container (driven under positive pressure)
28 $Co_2$ absorbent (adsorption) canister, calcium hydroxide or the like
29 feed port for circulation gas formed by adding oxygen gas and/or hydrogen gas to breathing gas (with $Co_2$ being reduced or eliminated therefrom) and various gas sensors or the like ($Co_2$ concentration, $O_2$ concentration, $H_2$ concentration, gas thermometer, hygrometer, pressure meter, etc.)
30 scavenging air blowing device
31 hydrogen gas leakage detection
32 supply device for suction-use oxygen gas and hydrogen gas (discharge into water) or discharge to canister side
33 breathing air suction-use detonation flame arrester unit (including a moistening device on the following stage)
34 air-suction-use detonation flame arrester unit (including various sensors, etc. on the preceding stage)

The invention claimed is:

1. A hydrogen-rich gas mixture breathing system, comprising:
    a breathing device;
    a suction air input passage fluidly connected to the breathing device to input a hydrogen-rich suction air to the breathing device;
    an oxygen gas or air supply fluidly connected to the suction air input passage that supplies oxygen gas or air;
    a hydrogen gas supply fluidly connected to the suction air input passage that supplies hydrogen gas;
    wherein the oxygen gas or air mixes with the hydrogen gas in the suction air input passage to generate the hydrogen-rich suction air with an amount of the hydrogen that exceeds an explosion threshold;
    a breathing air discharge passage fluidly connected to the breathing device to direct exhaled breathing air from the breathing device, the breathing air discharge passage including an outlet; and
    one of the following:
        a diluter in the breathing air discharge passage that is configured to dilute the exhaled breathing air with an inert gas or air to generate diluted exhaled breathing air with an amount of hydrogen that is equal to or less than the explosion threshold prior to discharge of the diluted exhaled breathing air from the outlet; or
        a combustor in the breathing air discharge passage that is configured to combust the exhaled breathing air to generate combusted exhaled breathing air and then discharge the combusted exhaled breathing air from the outlet wherein any portion of the breathing system in contact with hydrogen exceeding the explosion threshold comprises a structure that prevents explosion of the hydrogen gas.

2. The hydrogen-rich gas mixture breathing system of claim 1, further comprising:
    a flame arrester in the suction air input passage between the breathing device and the hydrogen gas supply, the flame arrester receiving the hydrogen-rich suction air; and
    a second flame arrester in the breathing air discharge passage between the breathing device and the outlet and receiving the exhaled breathing air.

3. The hydrogen-rich gas mixture breathing system of claim 1, further comprising a recirculation passage connecting the breathing air discharge passage and the suction air input passage, and a carbon dioxide absorbent in the recirculation passage through which the exhaled breathing air is directed to remove carbon dioxide from the exhaled breathing air.

4. The hydrogen-rich gas mixture breathing system of claim 1, further comprising a switching valve fluidly connected to the breathing device, the suction air input passage is fluidly connected to the switching valve;
an aerosol supply passage fluidly connected to the switching valve, and an aerosol supply fluidly connected to the aerosol supply passage that supplies an aerosol to the aerosol supply passage;
wherein the switching valve switches between the suction air input passage and the aerosol supply passage.

5. The hydrogen-rich gas mixture breathing system of claim 1, wherein the breathing device comprises a breathing mask.

6. The hydrogen-rich gas mixture breathing system of claim 1, wherein the hydrogen gas supply and the oxygen gas supply are combined or separate from each other.

7. The hydrogen-rich gas mixture breathing system of claim 4, further comprising a switching valve in the breathing air discharge passage, an aerosol discharge passage fluidly connected to the switching valve, and an aerosol capturing device in the aerosol discharge passage.

8. A hydrogen-rich gas mixture breathing system, comprising:
a breathing device;
a suction air input passage fluidly connected to the breathing device to input a hydrogen-rich suction air to the breathing device;
an oxygen gas or air supply fluidly connected to the suction air input passage that supplies oxygen gas or air;
a hydrogen gas supply fluidly connected to the suction air input passage that supplies hydrogen gas;
wherein the oxygen gas or air mixes with the hydrogen gas in the suction air input passage to generate the hydrogen-rich suction air with an amount of the hydrogen that exceeds an explosion threshold;
a flame arrester in the suction air input passage between the breathing device and the hydrogen gas supply, the flame arrester receiving the hydrogen-rich suction air;
a breathing air discharge passage fluidly connected to the breathing device to direct exhaled breathing air from the breathing device, the breathing air discharge passage including an outlet; and
a second flame arrester in the breathing air discharge passage between the breathing device and the outlet and receiving the exhaled breathing air wherein any portion of the breathing system in contact with hydrogen exceeding the explosion threshold comprises a structure that prevents explosion of the hydrogen gas.

9. The hydrogen-rich gas mixture breathing system of claim 8, further comprising a recirculation passage connecting the breathing air discharge passage and the suction air input passage, and a carbon dioxide absorbent in the recirculation passage through which the exhaled breathing air is directed to remove carbon dioxide from the exhaled breathing air.

10. The hydrogen-rich gas mixture breathing system of claim 8, further comprising a switching valve fluidly connected to the breathing device, the suction air input passage is fluidly connected to the switching valve;
an aerosol supply passage fluidly connected to the switching valve, and an aerosol supply fluidly connected to the aerosol supply passage that supplies an aerosol to the aerosol supply passage;
wherein the switching valve switches between the suction air input passage and the aerosol supply passage.

11. The hydrogen-rich gas mixture breathing system of claim 8, wherein the breathing device comprises a breathing mask.

12. The hydrogen-rich gas mixture breathing system of claim 8, wherein the hydrogen gas supply and the oxygen gas supply are combined or separate from each other.

13. The hydrogen-rich gas mixture breathing system of claim 10, further comprising a switching valve in the breathing air discharge passage, an aerosol discharge passage fluidly connected to the switching valve, and an aerosol capturing device in the aerosol discharge passage.

* * * * *